(12) United States Patent
Kolins

(10) Patent No.: US 8,336,790 B2
(45) Date of Patent: Dec. 25, 2012

(54) PERSONAL AROMATHERAPY DEVICE

(76) Inventor: Maria C. Kolins, Boca Raton, FL (US)

( * ) Notice: Subject to any disclaimer, the term of this patent is extended or adjusted under 35 U.S.C. 154(b) by 661 days.

(21) Appl. No.: 12/459,558

(22) Filed: Jul. 3, 2009

(65) Prior Publication Data

US 2010/0001093 A1   Jan. 7, 2010

Related U.S. Application Data

(60) Provisional application No. 61/133,850, filed on Jul. 3, 2008.

(51) Int. Cl.
*B65D 1/32* (2006.01)
(52) U.S. Cl. ........... 239/327; 239/39; 222/206; 222/207
(58) Field of Classification Search .............. 239/39, 239/327; 222/206, 207
See application file for complete search history.

(56) References Cited

U.S. PATENT DOCUMENTS

| | | | | |
|---|---|---|---|---|
| 3,306,499 A | * | 2/1967 | Lykes | 222/635 |
| 5,875,936 A | * | 3/1999 | Turbett et al. | 222/207 |
| 6,581,852 B2 | * | 6/2003 | Garcia et al. | 239/326 |
| 2003/0098362 A1 | * | 5/2003 | Chuang | 239/44 |
| 2006/0151535 A1 | * | 7/2006 | Duquet et al. | 222/183 |

* cited by examiner

*Primary Examiner* — Len Tran
*Assistant Examiner* — Joel Zhou
(74) *Attorney, Agent, or Firm* — Robert M. Downey, P.A.

(57) ABSTRACT

A personal device for releasing the aroma of an essential oil includes an inner flexible container received within a rigid outer shell that is open on opposite sides to expose side portions of the inner flexible container. An interior chamber of the flexible container is partially filled with cotton or other fibrous material and a charge of an essential oil that saturates the cotton material. A cap fitted to an open top end of the flexible container includes a flip nozzle with a ball valve. The flip nozzle is operable between a lowered position to close the ball valve and seal the open top of the flexible container closed, and a raised straight up position to open the ball valve and permit release of beneficial aromas of the essential oil from an open end of the nozzle upon squeezing the exposed sides of the flexible container while holding the nozzle below the user's nostrils so that the aromas are released for direct inhalation through the user's nostrils.

12 Claims, 3 Drawing Sheets

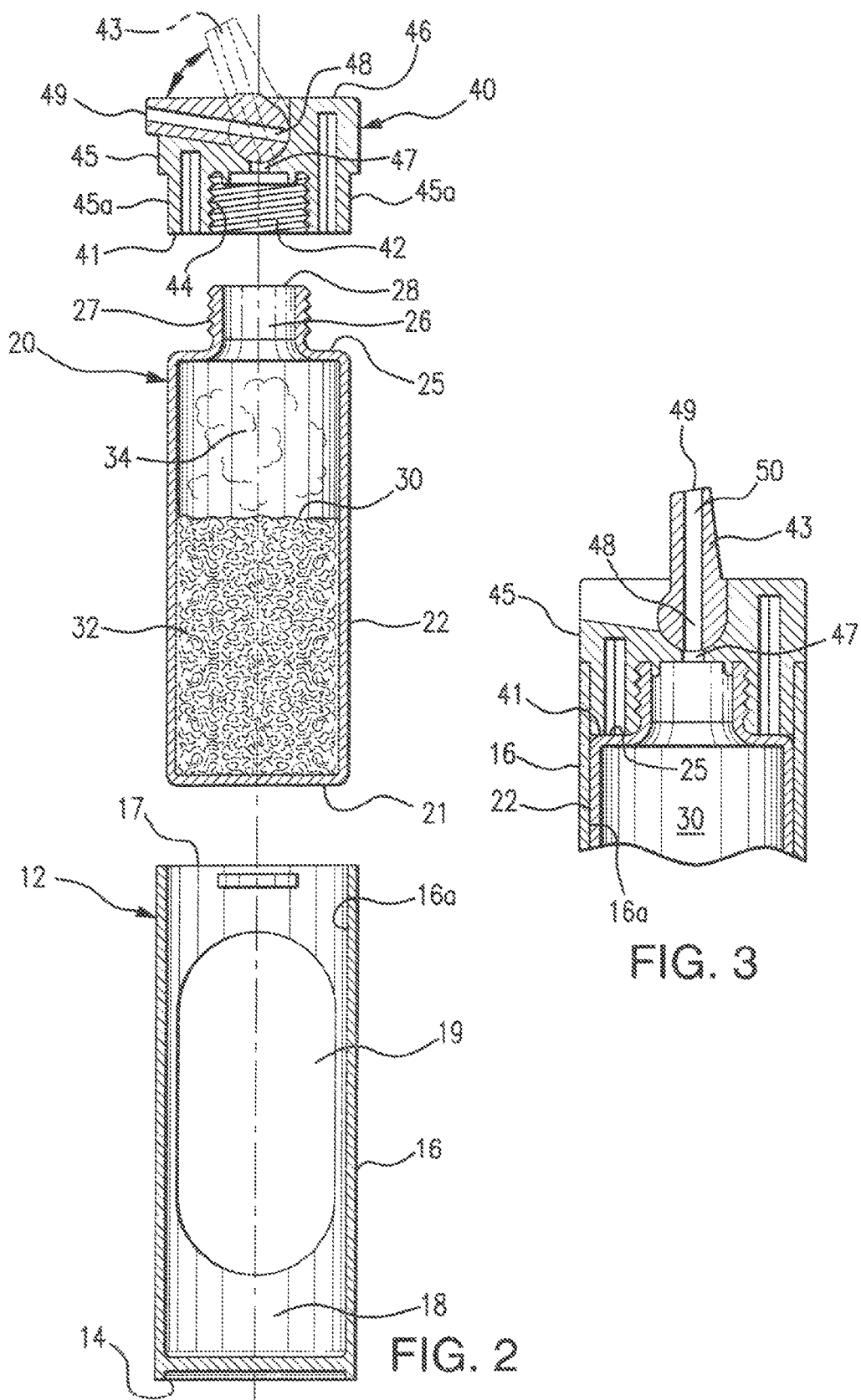

US 8,336,790 B2

PERSONAL AROMATHERAPY DEVICE

This application is based on provisional patent application Ser. No. 61/133,850 filed on Jul. 3, 2008.

BACKGROUND OF THE INVENTION

1. Field of the Invention

The present invention is directed to a small device for releasing the aroma of essential oils and, more particularly, to a personal aromatherapy device that is easily carried on one's person (e.g., purse or pocket) and includes a manually operated mechanism for selectively allowing release of aroma from an essential oil contained within the device.

2. Discussion of the Related Art

Essential oils are concentrated, hydrophobic liquids that contain volatile aroma compounds from aromatic plants. The term "essential" refers to the distinctive scent, or essence, of the plant. Various essential oils have been used medicinally at different periods throughout history. In recent decades, there has been an increased interest in the use of essential oils for aromatherapy. This popular method of natural treatment for health and wellness relies on the specific aromas carried by essential oils for the purpose of affecting a person's mood or health.

It has been found that the distinct aromas from different essential oils have specific benefits to a person's health and well-being. For instance, eucalyptus oil, in combination with peppermint oil, provides relief for the airways in case of cold or flu. Lavender oil is used to calm and relax a person, as well as to sooth headaches and migraines. Jasmine oil, sandalwood oil, and rose oil are all used as an aphrodisiac. Lemon oil has been found to be particularly beneficial as an anti-stress/anti-depressant. In a Japanese study, the aroma of lemon essential oil was found to reduce stress in mice. Researchers have also revealed that lemon oil aroma may enhance a person's mood and relax the person. The benefits of aromatherapy are based on the belief that essential oils contain a distillation of the "life force" of the plant from which it is derived that will "balance the energies" of the body and promote healing or well-being.

Presently, people wishing to derive the benefits of aromatherapy are required to visit a professional spa or make a substantial investment for in-home aromatherapy. And, while small containers are available for holding essential oils, there is presently no suitable personal aromatherapy device that can be conveniently carried in one's pocket or purse and used without spilling the essential oil. More particularly, there remains a definite need for a small, stylish personal aromatherapy device that can be conveniently and discretely pulled from one's pocket or purse and easily operated with one hand (i.e., using two fingers) to release the beneficial aroma of an essential oil carried in the device. There is a further need for a personal aromatherapy device that can be opened for use and sealed with a single finger operation and placed back in one's purse or pocket.

OBJECTS AND ADVANTAGES OF THE PRESENT INVENTION

Considering the foregoing, it is a primary object of the present invention to provide a personal aromatherapy device that can be conveniently carried on one's person (e.g., in a purse or pocket) and discretely removed for personal use by selectively and temporarily opening a normally sealed aroma release nozzle or opening on the top of the device, and wherein the device can be sealed closed after use and replaced in one's purse or pocket without spilling the essential oil contained therein.

It is a further object of the present invention to provide a personal aromatherapy device that is small, stylish and easy to carry in one's purse, pocket, briefcase or other article worn or carried by the user.

It is still a further object of the present invention to provide a personal aromatherapy device that is relatively inexpensive and disposable.

It is still a further object of the present invention to provide a personal aromatherapy device, as described above, which releases a beneficial aroma of an essential oil directly below the nose for inhalation through the user's nostrils, and without affecting other persons nearby the user.

These and other objects and advantages of the present invention are more readily apparent with reference to the detailed description and accompanying drawings.

SUMMARY OF THE INVENTION

The present invention is directed to a personal aromatherapy device. The device includes an outer rigid shell with opposite side openings or windows and an inner flexible container received within the outer shell so that a portion of the opposite sides of the flexible container are exposed by the side openings of the rigid outer shell. The flexible container includes an open top communicating with an interior chamber. The interior chamber is at least partially filled with cotton or other fibrous material and a charge of an essential oil that saturates the cotton material. A cap is received by the top of the outer rigid shell and attaches to the screw threads of the inner flexible container. A port located at the top of the inner screw threads of the cap connects the interior of the inner flexible container to a nozzle and ball joint, through which the aromas located within the interior chamber can escape. The nozzle and ball joint are operable between a horizontal, closed position and a vertical, open position. While the nozzle is in the closed position, aromas and/or liquids may not escape the inner chamber. While in the open position, aromas may escape the inner chamber. The rate of release of aromas from the inner chamber is dependent on the force put on the sides of the device. If squeezed lightly, a lighter amount of aroma will be released. In use, the open nozzle is held directly below the users nose (e.g., approximately 1-4 inches below the nostrils) and the flexible sides are squeezed to release the beneficial aromas of the essential oil for direct inhalation through the user's nostrils without affecting other persons in the vicinity of the user.

BRIEF DESCRIPTION OF THE DRAWINGS

For a fuller understanding of the nature of the present invention, reference should be made to the following detailed description taken in conjunction with the accompanying drawings in which:

FIG. 2 is an exploded elevational view in cross section showing the primary component parts of the personal aromatherapy device;

FIG. 3 is an isolated cross-sectional view showing a cap fitted to a top neck of a flexible container of the device with a flip nozzle moved to a raised position to open a ball valve on the flip nozzle, thereby aligning a port of the nozzle in open communication with an open top end of the neck of the flexible container.

Like reference numerals refer to like parts throughout the several views of the drawings.

DETAILED DESCRIPTION OF THE PREFERRED EMBODIMENTS

Figure 1:
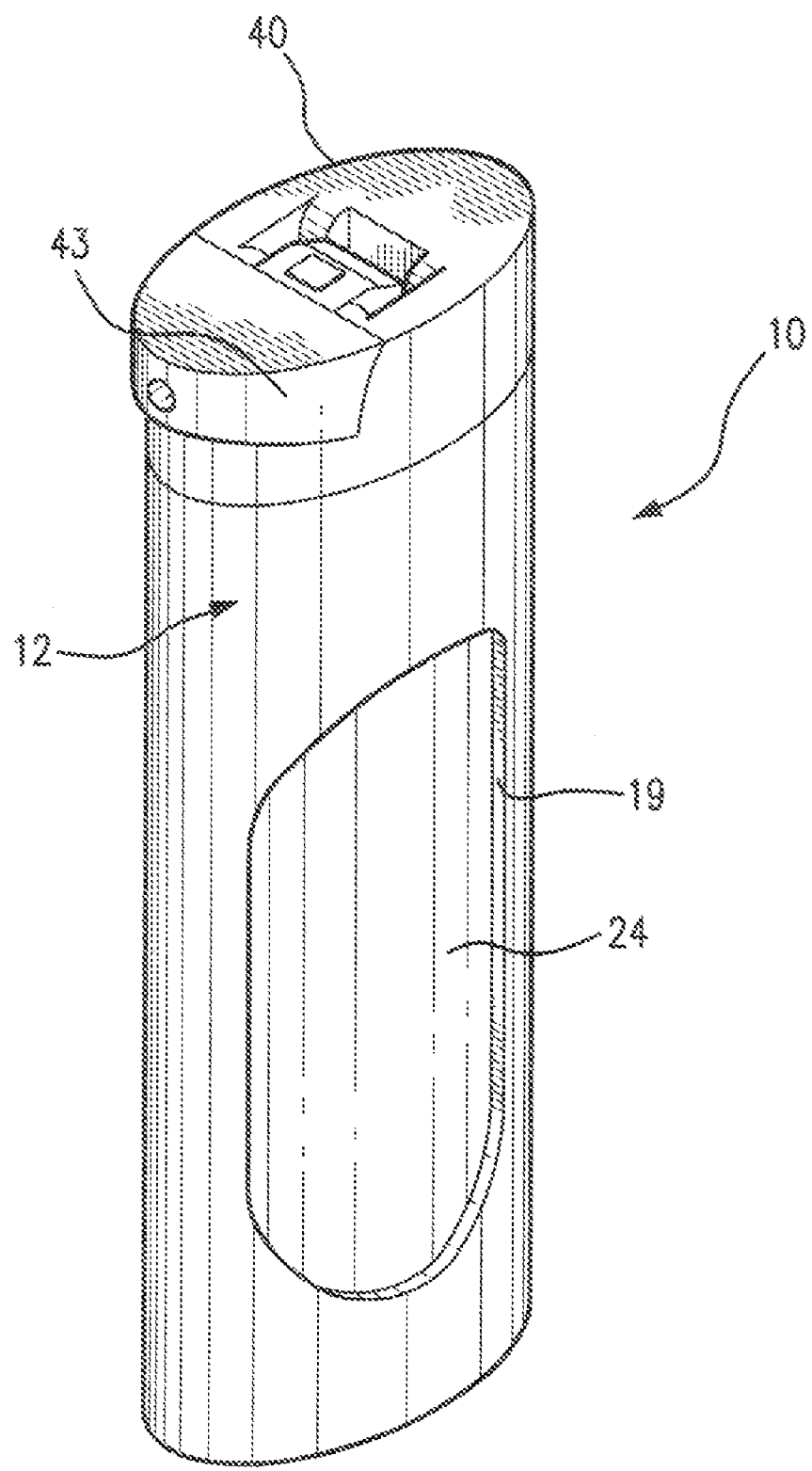
FIG. 1 is a top, front perspective view of the personal aromatherapy device of the present invention.
Figure 4:
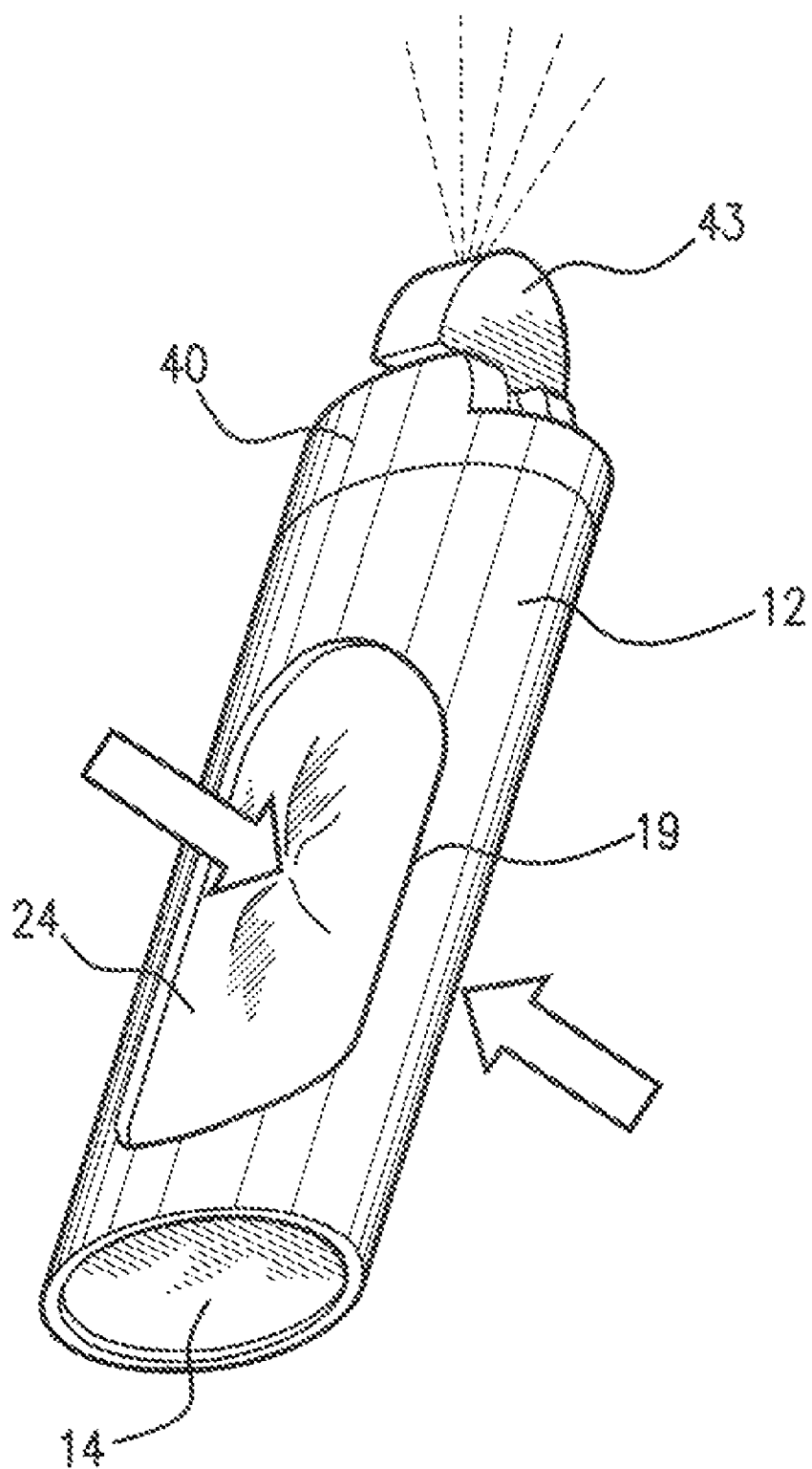
FIG. 4 is a bottom, front perspective view of the personal aromatherapy device demonstrating inward pressure, by squeezing, on opposite flexible sidewall portions of the container to thereby urge the beneficial aromas of an essential oil outwardly from the open port of the top nozzle.

Referring to FIGS. 1-4, the personal aromatherapy device is shown and is generally indicated as 10. The personal aromatherapy device 10 includes an outer shell 12 formed of a rigid material (e.g., molded plastic) having a bottom 14, a surrounding sidewall 16, an open top 17, and a hollow interior 18. Window openings 19 expose the interior of the shell on opposite sides of the surrounding wall structure 16.

The personal aromatherapy device 10 further includes an inner container 20 formed at least partially of a flexible material (e.g., a rubber or elastomeric composition). The inner container 20 has a bottom 21, a surrounding sidewall 22 that includes opposite sidewall exterior surfaces 24, and a neck 26 extending from a top end 25 of the inner container. An exterior of the neck 26 is provided with screw threads 27. The neck 26 has an open top 28 communicating with an interior chamber 30 that is at least partially filled with a cotton material 32 or other fibrous material, and a charge of a particular essential oil. The essential oil at least partially saturates within the interior chamber 30 and releases vapors 34 that carry a beneficial aroma. The cotton/fibrous material 32 holds the liquid essential oil, thereby preventing the oil from moving freely about the interior chamber 30 and possibly leaking from the top of the device 10.

The personal aromatherapy device 10 further includes a cap 40 formed of a rigid material (i.e. molded plastic) having a bottom 41, a sidewall 45 and a top 46. The bottom 41 of the cap 40 has a central bore 42 surrounded by internal screw threads 44 for receiving external screw threads 27 in order to attach the cap 40 to the top neck 26 of the inner container 20. Above the bore 42 there is a small opening 47. An outer lower side surface 45a of the cap 40 is of reduced dimension for receipt within the open top of the outer shell 12 thereby providing a flush outer side surface to the personal aromatherapy device 10.

Fitted into the top of cap 40 is a flip nozzle 43 with a ball valve 48 which also connects to the small opening 47 for transfer of beneficial aromas. The flip nozzle 43 is operable between a lowered position to close the ball valve and seal the open top 28 of the flexible container 20 closed, and a raised straight up position to open the ball valve 48 and permit release of beneficial aromas of the essential oil through a tubular port 50 and out from an open end of the nozzle 43 upon squeezing the exposed sides 24 of the flexible container 20 while holding the nozzle 43 below the user's nostrils.

As seen in FIGS. 2 and 3, the interior dimensions of the hollow interior 18 are generally congruent with the exterior dimensions of the interior chamber 20 so that the surrounding sidewall 22 of the inner container 20 is pressed against the inner sidewall surface 16a of the outer rigid shell 12 and the top end 25 of the inner container 20 is in contact with the bottom 41 of the cap 40. This allows the opposite sidewall exterior surfaces 24 to fill and close the window openings 19 of the outer rigid shell 12 so that the opposite sidewall exterior surfaces 24 are exposed for application of an external, inwardly directed squeezing force. Furthermore, the pressed fit of the exterior surface of the inner container 20 against the inner sidewall surface 16a of the outer rigid shell 20 leaves no gaps between the sidewall exterior surface of the inner container 20 and the inner sidewall surface 16a of the outer rigid shell 12.

In use, the inwardly directed squeezing or pressing force is exerted on the opposite sidewall exterior surfaces 24 that are exposed by the window openings 19 of the outer rigid shell 12. The inwardly directed pressing force urges the vapors and aroma of the essential oil outwardly from the tubular port when the ball valve 48 is in the open position.

While the invention has been described and illustrated in accordance with a preferred and practical embodiment thereof, it is recognized that departures from the instant disclosure are fully contemplated within the spirit and scope of the invention which is not limited except as defined in the following claims as interpreted under the Doctrine of Equivalents.

What is claimed is:

1. A personal aromatherapy device comprising:
    a container including a bottom, a top end, a flexible and resilient surrounding sidewall extending between said bottom and said top end, and an opening proximate said top end communicating with an interior chamber, and said flexible and resilient surrounding sidewall including at least one sidewall exterior surface structured and disposed for applying an external inwardly directed pressing force thereto;
    an outer shell formed of a rigid material and including a surrounding sidewall structure, an open top, an inner surface surrounding a hollow interior for receiving said container therein, and said outer shell further including at least one window opening through said sidewall structure, and said at least one window opening including a surrounding peripheral edge;
    said inner surface of said outer shell being congruent with said flexible and resilient surrounding sidewall of said container so that said flexible and resilient surrounding sidewall is pressed against said inner surface of said outer shell with said at least one sidewall exterior surface of said container completely in contact with said surrounding peripheral edge of said at least one window opening and completely closing said at least one window opening and said at least one sidewall exterior surface exposed for application of said external inwardly directed pressing force thereto;
    a fibrous material at least partially filled within said interior chamber and at least partially saturated with an essential oil that releases vapors carrying an aroma;
    a cap for covering said opening of said container and said cap including an outer lower side surface for receipt through said open top of said outer shell and into said hollow interior;
    a valve member with a closable and sealable port communicating with said opening of said container and said interior chamber, and said valve member being operable between a closed position to seal the port closed, thereby preventing release of the vapors and aroma of the essential oil from said interior chamber, and said valve member being further operable to an open position for opening said port and permitting release of the vapors and aroma of the essential oil outwardly from said port and into the ambient air surrounding a user's nostrils; and
    wherein application of the inwardly directed pressing force on said at least one sidewall exterior surface exposed through said window opening urges the vapors and aroma of the essential oil outwardly from said port when said valve member is in said open position.

2. The personal aromatherapy device as recited in claim 1 wherein said fibrous material is partially filled within said interior chamber to provide an empty space above said fibrous material for accumulation of the vapors of the essential oil prior to release from said interior chamber and out from said port.

3. The aromatherapy device as recited in claim 1 wherein said valve member includes a ball valve.

4. The aromatherapy device as recited in claim 3 wherein said valve member further includes a flip nozzle integrally formed with said ball valve and extending therefrom, said flip nozzle including a tubular passage extending therethrough and defining said port, and said flip nozzle being operably moveable between a lowered position to close said ball valve and a raised position to open said ball valve and thereby permitting release of the vapors and aroma outwardly from said port of said flip nozzle.

5. The personal aromatherapy device as recited in claim 4 further comprising:
- a top neck on said top of said container and including said opening, and said neck including screw threads formed about an exterior, and
- said cap including interior screw threads surrounding an open bore in a bottom of said cap for receipt of said neck therein and threaded engagement of said interior screw threads with said exterior screw threads on said neck to thereby attach said cap to said container.

6. The personal aromatherapy device as recited in claim 1 wherein said fibrous material is cotton.

7. The personal aromatherapy device as recited in claim 1 wherein said flexible and resilient surrounding sidewall of said container includes two oppositely disposed sidewall exterior surfaces structured and disposed for applying the inwardly directed pressing force thereto, and said outer shell includes two of said window openings on opposite sides of said outer shell for exposing the two oppositely disposed sidewall exterior surfaces of said container to allow for application of the internal inward pressing force thereto, and thereby urging the vapors and essential oil outwardly from said port when said valve is in said open position.

8. A personal aromatherapy device comprising:
- an inner container formed at least partially of a flexible material and including a bottom, a surrounding sidewall formed of a flexible, resilient material, a top end, a neck extending upwardly from said top end and terminating at an open top in communication with an interior chamber, and said flexible and resilient surrounding sidewall including two oppositely disposed exterior surfaces structured and disposed for applying an external inwardly directed pressing force thereto;
- an outer shell formed of a rigid material and including a surrounding sidewall structure, an open top, and inner surface surrounding a hollow interior for receiving said inner container therein, and said outer shell further including two window openings on opposite sides thereof, and said two window openings each including a surrounding peripheral edge;
- said surrounding sidewall of said inner container being congruent with said inner surface of said outer shell so that said surrounding sidewall of said inner container is pressed against the inner surface of said outer shell and said two oppositely disposed exterior surfaces of said inner container are completely in contact with said surrounding peripheral edge of said window openings and completely fill and close said window openings of said outer shell with said oppositely disposed exterior surfaces exposed for application of said external inwardly directed pressing force thereto;
- a fibrous material at least partially filled within said interior chamber of said inner container and said fibrous material being at least partially saturated with an essential oil that releases vapors carrying an aroma;
- a cap fitted to said neck of said inner container in sealed engagement therewith and said cap including an outer lower side surface for receipt through said open top of said outer shell and into said hollow interior;
- a valve member on said cap and including a port communicating with said open top of said neck and said interior chamber, and said valve member being operable to a closed position to seal said port closed, thereby preventing release of the vapor and aroma of the essential oil outwardly from said interior chamber, and said valve member being further operable to an open position wherein said port is disposed in open communicating relation with said open top of said neck and said interior chamber for allowing release of the vapors and aroma of the essential oil outwardly from said interior chamber and through said port; and
- wherein application of the inwardly directed pressing force on the oppositely disposed exterior surfaces of said flexible and resilient surrounding sidewall of said inner container exposed through said two window openings urges the vapors and aroma of the essential oil outwardly from said port when said valve member is in said open position.

9. The personal aromatherapy device as recited in claim 8 wherein said fibrous material is partially filled within said interior chamber of said inner container to provide an empty space within said interior chamber, above said fibrous material, for accumulation of the vapors of the essential oil prior to release from said interior chamber and out from said port.

10. The personal aromatherapy device as recited in claim 9 wherein said valve member includes a ball valve.

11. The personal aromatherapy device as recited in claim 10 wherein said valve member further includes a flip nozzle integrally formed with said ball valve and extending therefrom, said flip valve including a tubular passage extending therethrough and defining said port, and said flip nozzle being operably moveable between a lowered position to close said ball valve and a raised position to open said ball valve and thereby permitting release of the vapors and the aroma outwardly from said port of said flip nozzle.

12. The personal aromatherapy device as recited in claim 11 wherein said fibrous material is cotton.

* * * * *